(12) United States Patent
Shu et al.

(10) Patent No.: US 10,633,364 B2
(45) Date of Patent: Apr. 28, 2020

(54) CRYSTALS OF QUINAZOLINE DERIVATIVE AND PREPARATION METHOD THEREFOR

(71) Applicant: Xuanzhu Pharma Co., Ltd., Jinan, Shandong Province (CN)

(72) Inventors: Chutian Shu, Jinan (CN); Jinyuan Wang, Jinan (CN); Zhenhua Wang, Jinan (CN)

(73) Assignee: XUANZHU PHARMA CO., LTD., Shandong Province (CN)

( * ) Notice: Subject to any disclaimer, the term of this patent is extended or adjusted under 35 U.S.C. 154(b) by 0 days.

(21) Appl. No.: 16/065,880

(22) PCT Filed: Dec. 23, 2016

(86) PCT No.: PCT/CN2016/111767
§ 371 (c)(1),
(2) Date: Nov. 13, 2018

(87) PCT Pub. No.: WO2017/107985
PCT Pub. Date: Jun. 29, 2017

(65) Prior Publication Data
US 2019/0135779 A1 May 9, 2019

(30) Foreign Application Priority Data
Dec. 25, 2015 (CN) .......................... 2015 1 0996543

(51) Int. Cl.
*A61P 11/00* (2006.01)
*A61P 35/00* (2006.01)
*C07D 401/12* (2006.01)
*A61K 31/517* (2006.01)

(52) U.S. Cl.
CPC .......... *C07D 401/12* (2013.01); *A61K 31/517* (2013.01); *A61P 11/00* (2018.01); *A61P 35/00* (2018.01); *C07B 2200/13* (2013.01)

(58) Field of Classification Search
CPC ................................ A61P 11/00; A61P 35/00
See application file for complete search history.

(56) References Cited

U.S. PATENT DOCUMENTS

2013/0184297 A1* 7/2013 Huang ................. C07D 403/14
514/266.22
2014/0161801 A1 6/2014 Wu et al.

FOREIGN PATENT DOCUMENTS

| CN | 102382065 A | 3/2012 |
| CN | 103965119 A | 8/2014 |
| JP | 2013-53623 A | 9/2013 |
| WO | 2012/027960 A1 | 3/2012 |
| WO | 2012/159457 A1 | 11/2012 |

OTHER PUBLICATIONS

Wang, X., et al. "The potential of panHER inhibition in cancer." Frontiers in Oncology. (Jan. 28, 2015), vol. 5, Article 2, pp. 1-12. (Year: 2015).*
Lee, C.K., et al. "Impact of EGFR Inhibitor in Non-Small Cell Lung Cancer on Progression-Free and Overall Survival: A Meta-Analysis." JNCI. (May 1, 2013), vol. 105, Issue 9, pp. 595-605. (Year: 2013).*
Roskoski, R. "The ErbB/HER family of protein-tyrosine kinases and cancer." Pharmacological Research. (2014), vol. 79, pp. 34-74. (Year: 2014).*
Spector, N., et al. "Small molecule HER-2 tyrosine kinase inhibitors." Breast Cancer Research (2007), vol. 9, pp. 1-8 of 8. (Year: 2007).*
Navigating Cancer. "List of Cancer Chemotherapy Drugs." (2013). Accessed Nov. 26, 2013. Available from: < https://www.navigatingcare.com/library/all/chemotherapy_drugs >. (Year: 2013).*
International Search Report dated Mar. 28, 2017, issued in International Application No. PCT/CN2016/111767, filed Dec. 23, 2016, 7 pages.
Ashizawa, K., "Salt and Crystal Form Optimization and Crystallization Technology," Pharm Tech Japan, 18(10): 81-96, 2002.
Extended European Search Report dated Jun. 3, 2019, issued in corresponding European Application No. 16877795.1, filed Dec. 23, 2016, 4 pages.

(Continued)

*Primary Examiner* — Noble E Jarrell
*Assistant Examiner* — John S Kenyon
(74) *Attorney, Agent, or Firm* — Christensen O'Connor Johnson Kindness PLLC

(57) ABSTRACT

The invention relates to Crystal form I and Crystal form II of dihydrochloride of N-(4-((3-chloro-4-fluorophenyl)amino)-7-((7-methyl-7-azaspiro[3.5]nonan-2-yl)methoxy)quinazolin-6-yl)acrylamide represented by the following Formula (I), and preparation methods therefor, wherein the Crystal form I has an X-ray powder diffraction pattern having characteristic peaks at the 2θ positions of 6.0±0.2°, 7.3±0.2°, 11.7±0.2°, 12.9±0.2°, 18.4±0.2°, 24.7±0.2°, and 26.3±0.2°, as determined by using Cu-Kα radiation, and the Crystal form II has an X-ray powder diffraction pattern having characteristic peaks at the 2θ positions of 5.0±0.2°, 7.0±0.2°, 10.1±0.2°, 17.0±0.2°, 26.0±0.2°, and 26.5±0.2°, as determined by using Cu-Kα radiation.

(I)

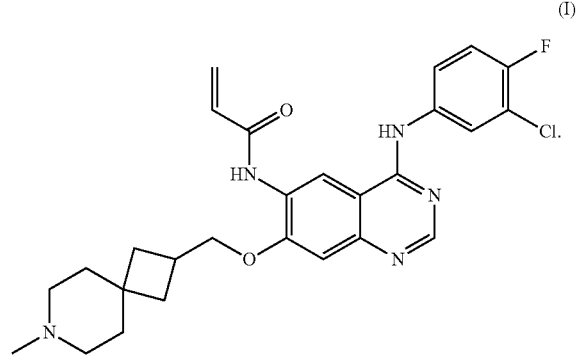

20 Claims, 4 Drawing Sheets

(56) References Cited

OTHER PUBLICATIONS

"From Pharmaceutical Synthesis to Production," Process Chemistry, Mar. 30, 2014, pp. 405-413, 420-429 and 446-451.
Hirayama, R., "Organic Compound Crystal Preparation Handbook," 2008, pp. 17-23, 37-40, 45-51, and 57-65.
Notice of Reasons for Rejection dated May 28, 2019, issued in Japanese Application No. 2018-533210, filed Nov. 25, 2016, 6 pages.
Wermuth, C.G., "The Practice of Medicinal Chemistry," Technomics, Inc., 1999, pp. 347-365.
Ashara, S., "Solvent Handbook," Kodansha, Ltd., pp. 47-51, 1985.
Decision of Final Rejection dated Oct. 8, 2019, issued in corresponding Chinese Application No. 2018-533210, filed Dec. 23, 2016, 6 pages.

* cited by examiner

CRYSTALS OF QUINAZOLINE DERIVATIVE AND PREPARATION METHOD THEREFOR

TECHNICAL FIELD

The present invention relates to crystals of dihydrochloride of N-(4-((3-chloro-4-fluorophenyl)amino)-7-((7-methyl-7-azaspiro[3.5]nonan-2-yl)methoxy)quinazolin-6-yl)acrylamide, preparation methods and uses thereof.

BACKGROUND ART

Protein tyrosine kinases (PTKs) are a class of enzymes that can catalytically transfer a phosphate group from ATP to the tyrosine residue of a protein substrate, and play a role in normal cell growth. Many growth factor receptor proteins work via tyrosine kinases, and affect signal transduction pathways through this process, thereby modulating cell growth. However, under some conditions, these receptors become abnormal due to either mutation or over-expression, cause uncontrolled cell proliferation, lead to tumor growth, and finally result in a well-known disease—cancer. Growth factor receptor protein tyrosine kinase inhibitors play a role in treatment of cancer and other diseases characterized by uncontrolled or abnormal cell growth, by inhibiting said phosphorylation process.

Epidermal growth factor receptor (EGFR) is a multifunctional glycoprotein that is widely distributed on the cell membranes of various tissues in human body, and is an avian erythroblastic leukemia viral (v-erb-b) oncogene homolog. Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). Clinical studies show that EGFR and the like are over-expressed in many tumors, for example, epithelial-derived tumors such as squamous cell carcinoma of head and neck, breast cancer, rectal cancer, ovarian cancer, prostate cancer, and non-small cell lung cancer. By competing with ATP for binding kinase catalytic sites in the intracellular region, Pan-HER tyrosine kinase inhibitors block the autophosphorylation of tyrosine in the molecule, block the activation of tyrosine kinase, and inhibit the activation of HER family, thereby inhibiting cell cycle progression, accelerating cell apoptosis, and exerting a therapeutic action.

After binding to ligand, EGFR forms a dimer with a subgroup of HER family, and then binds to ATP to activate the tyrosine kinase activity of EGFR itself, resulting in the autophosphorylation at several tyrosine sites of the intracellular kinase region. Pan-HER tyrosine kinase inhibitors have good effect of inhibiting tumor growth, by acting on EGFR and HER2/4 simultaneously and inhibiting the activation of HER family.

The quinazoline derivative of the following Formula (I), N-(4-((3-chloro-4-fluorophenyl)amino)-7-((7-methyl-7-azaspiro[3.5]nonan-2-yl)methoxy)quinazolin-6-yl)acrylamide (which was disclosed in the patent application WO2012027960A1), is an irreversible Pan-HER tyrosine kinase inhibitor, can effectively inhibit EGFR, and also has an inhibitory effect on HER2/4. The drug having an irreversible inhibitory effect on HER/ErbB family can not only enhance the activity of drug, but also can reduce the generation of drug resistance, and has a significantly inhibitory effect on erlotinib-resistant H1975 cell line.

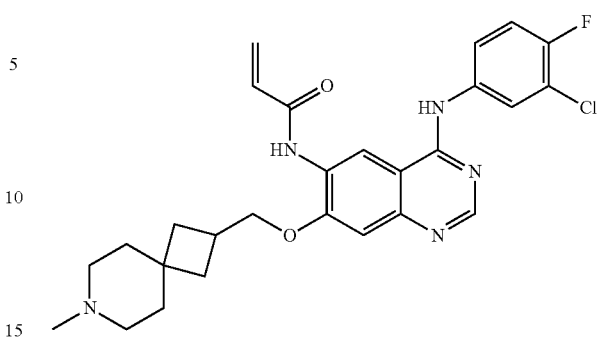

Formula (I)

Development of crystals is very important in drug development. Different forms of a compound have different bioavailability and solubility. Crystal forms have a great influence on the stability, processing property, bioavailability, solubility, formulation, and industrial production and transportation of compounds.

CONTENTS OF INVENTION

The purpose of the invention is to provide crystals of dihydrochloride of N-(4-((3-chloro-4-fluorophenyl)amino)-7-((7-methyl-7-azaspiro[3.5]nonan-2-yl)methoxy)quinazolin-6-yl)acrylamide of the Formula (I), and preparation methods and uses thereof. In order to achieve the purpose, the inventors conducted deep researches, and surprisingly found that a class of crystals of dihydrochloride of N-(4-((3-chloro-4-fluorophenyl)amino)-7-((7-methyl-7-azaspiro[3.5]nonan-2-yl)methoxy)quinazolin-6-yl)acrylamide represented by the Formula (I) had very excellent stability and pharmacokinetics, and therefore accomplished the invention.

In particular, the invention relates to the following technical solutions.

(1) Crystal form I of dihydrochloride of N-(4-((3-chloro-4-fluorophenyl)amino)-7-((7-methyl-7-azaspiro[3.5]nonan-2-yl)methoxy)quinazolin-6-yl)acrylamide represented by Formula (I), has the following crystal structure: an X-ray powder diffraction pattern having characteristic peaks at the 2θ positions of 6.0±0.2°, 7.3±0.2°, 11.7±0.2°, 12.9±0.2°, 18.4±0.2°, 24.7±0.2°, and 26.3±0.2°, as determined by using Cu-Kα radiation,

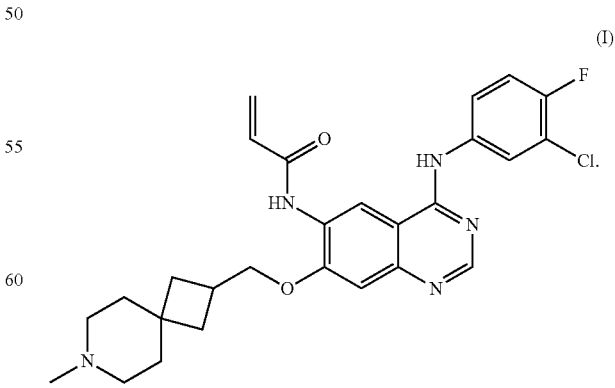

(I)

(2) The Crystal form I according to Item (1), has the following crystal structure: the X-ray powder diffraction pattern further having characteristic peaks at the 2θ positions of 16.0±0.2°, 18.7±0.2°, and 21.9±0.2°, as determined by using Cu-Kα radiation.

(3) The Crystal form I according to Item (2), has the following crystal structure: the X-ray powder diffraction pattern further having characteristic peaks at the 2θ positions of 16.6±0.2°, 20.0±0.2°, 24.3±0.2°, 28.1±0.2°, 28.5±0.2°, 29.2±0.2°, and 39.6±0.2°, as determined by using Cu-Kα radiation.

(4) The Crystal form I according to Item (1), has a first endothermic conversion peak at 109-188.5° C., and a second endothermic conversion peak at 188.5-215° C., as determined by differential scanning calorimetry (DSC).

(5) The Crystal form I according to Item (1), is a hydrate having a water content of 2%-3.5%, preferably 2.5%-3.2%, more preferably 2.9%-3.2%, most preferably 2.9%-3.0%.

(6) The Crystal form I according to Item (1), is a monohydrate.

(7) Crystal form II of dihydrochloride of N-(4-((3-chloro-4-fluorophenyl)amino)-7-((7-methyl-7-azaspiro[3.5]nonan-2-yl)methoxy)quinazolin-6-yl)acrylamide represented by Formula (I), has the following crystal structure: an X-ray powder diffraction pattern having characteristic peaks at the 2θ positions of 5.0±0.2°, 7.0±0.2°, 10.1±0.2°, 17.0±0.2°, 26.0±0.2°, and 26.5±0.2°, as determined by using Cu-Kα radiation.

(8) The Crystal form II according to Item (7), has the following crystal structure: the X-ray powder diffraction pattern further having characteristic peaks at the 2θ positions of 10.1±0.2°, 18.1±0.2°, 19.1±0.2°, 19.9±0.2°, and 24.9±0.2°, as determined by using Cu-Kα radiation.

(9) The Crystal form II according to Item (8), has the following crystal structure: the X-ray powder diffraction pattern further having characteristic peaks at the 2θ positions of 21.3±0.2°, 22.1±0.2°, 27.6±0.2°, 29.3±0.2°, and 35.8±0.2°, as determined by using Cu-Kα radiation.

(10) The Crystal form II according to Item (7), has a first endothermic conversion peak at 57-114.3° C., a second endothermic conversion peak at 114.5-175° C., and a third endothermic conversion peak at 188.4-199.4° C., as determined by differential scanning calorimetry (DSC).

(11) The Crystal form II according to Item (7), is a hydrate having a water content of 8.5%-14%, preferably 9%-13.5%, more preferably 10%-13%, most preferably 11%-12%.

(12) The Crystal form II according to Item (7), is a hydrate containing 3-5 molecules of water.

In addition, the invention further provides a method for preparing Crystal form I or Crystal form II of dihydrochloride of a compound of Formula (I), wherein the amorphous compound of Formula (I) used can be synthesized by the method as disclosed in WO2012027960A1.

(13) A method for preparing the Crystal form II, comprising the following steps: a free base of N-(4-((3-chloro-4-fluorophenyl)amino)-7-((7-methyl-7-azaspiro[3.5]nonan-2-yl)methoxy)quinazolin-6-yl)acrylamide, compound of Formula (I), is dissolved in water or a mixed solvent of water and an organic solvent, subjected to addition of concentrated hydrochloric acid to produce a solution, and the solution is filtrated and dried to obtain the Crystal form II.

The method preferably comprises the following steps: a free base of a compound of Formula (I) is suspended in water, and is dissolved by adding concentrated hydrochloric acid to produce a solution, then the solution is subjected to precipitation at room temperature, and then is filtrated and dried to obtain Crystal form II. The concentrated hydrochloric acid preferably has a concentration of 12 mol/L.

(14) A method for preparing the Crystal form I, wherein Crystal form II is dried in vacuum to obtain Crystal form I.

The vacuum has a condition as followed: at a pressure of −1.0×10³ KPa and a temperature of 35-40° C., and for a period of 3-8 h.

(15) A method for preparing the Crystal form II, comprising the following steps: Crystal I is dissolved in water or a mixed solvent of water and an organic solvent to produce a solution, and the solution is filtrated and dried to obtain Crystal form II.

(16) The method for preparing the Crystal form II according to Item (13) or (15), wherein the organic solvent is selected from the group consisting of a lower alcohol organic solvent, a lower cyclic ether organic solvent, a lower ketone organic solvent and a lower nitrile organic solvent.

The lower alcohol organic solvent is preferably methanol, ethanol, isopropanol or n-butanol; the lower cyclic ether organic solvent is preferably tetrahydrofuran or dioxane; the lower ketone organic solvent is preferably acetone, butanone or methyl isobutyl ketone, more preferably acetone; the lower nitrile organic solvent is preferably acetonitrile.

(17) The method for preparing the Crystal form II according to Item (13) or (15), wherein the mixed solvent of water and an organic solvent refers to a mixed solvent of water and an organic solvent at a certain ratio by volume, preferably, a mixed solvent of water and a lower alcohol organic solvent, a lower cyclic ether organic solvent, a lower ketone organic solvent or a lower nitrile organic solvent at any ratio by volume, including, but not limited to the following mixed solvent systems and ratios: methanol/water (10:1, 5:1 or 3:1), ethanol/water (10:1, 5:1 or 3:1), acetonitrile/water (10:1, 5:1 or 3:1), tetrahydrofuran/water (10:1, 5:1 or 3:1), acetone/water (10:1, 8:1, 5:1, 4:1 or 3:1), 1,4-dioxane/water (10:1, 5:1 or 3:1) etc., more preferably, a mixed solvent of acetone/water.

Crystal form I and Crystal form II of dihydrochloride of a compound of Formula (I) as prepared in the invention have good solubility in water, a buffer or an organic solvent, which is favorable for use in manufacture of a medicament.

In addition, Crystal form I and Crystal form II of dihydrochloride of a compound of Formula (I) as prepared in the invention have good stability, can be prepared by simple processes, have stable quality, have good physicochemical property, and can be produced industrially on a large scale.

Furthermore, Crystal form I and Crystal form II of dihydrochloride of a compound of Formula (I) as prepared in the invention have better efficacy, longer half-life, and higher drug exposure in animal compared with its amorphous form.

SPECIFIC MODES FOR CARRYING OUT THE INVENTION

Figure 1:
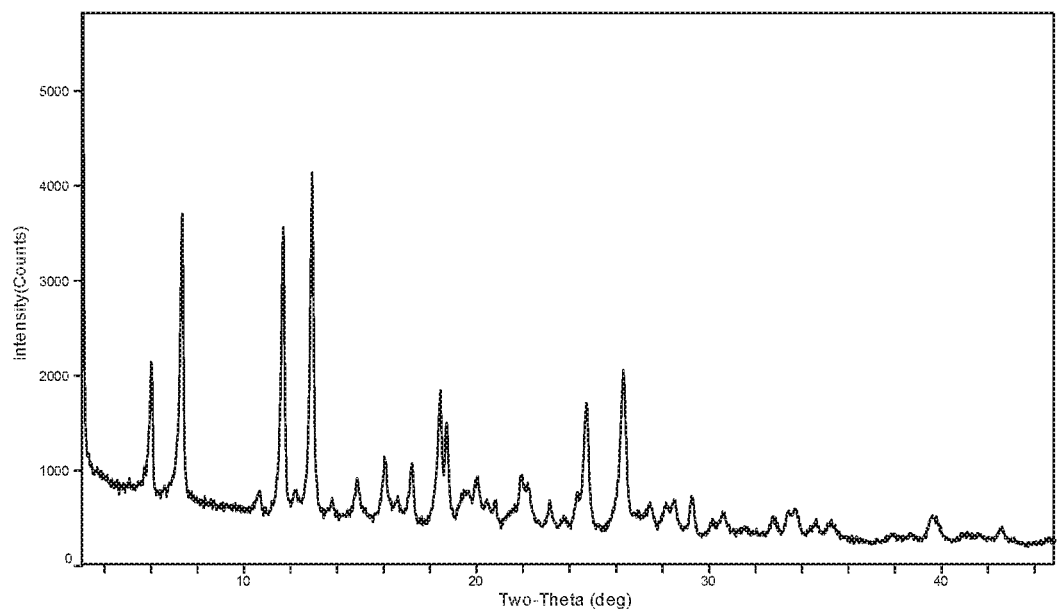
FIG. 1 shows the X-ray powder diffraction (XRPD) pattern of Crystal form I of dihydrochloride of a compound of Formula (I), wherein the ordinate represents diffraction intensity (CPS), and the abscissa represents the diffraction angle (2θ).

In the description and claims of the present application, a compound is denominated based on its chemical structural formula. If the name of a compound used herein is not consistent with the chemical structural formula, the chemical structural formula or chemical formula will prevail.

In the present application, unless otherwise specified, the scientific and technical terms used herein have the meanings as generally understood by a person skilled in the art. However, in order to understand the invention better, definitions and explanations are provided for a part of relevant terms. In addition, if the definitions and explanations of the terms provided in the present application are different from the meanings generally understood by a person skilled in the art, the definitions and explanations of the terms provided in the present application shall prevail.

The term "organic solvent" as used in the invention may refer to any commercially available organic solvent, or a mixed solvent. The mixed solvent refers to a mixed solvent consisting of two or more organic solvents at a certain ratio by volume, or a mixed solvent consisting of an organic solvent and water at a certain ratio by volume, preferably, a mixed solvent of water and a lower alcohol organic solvent, a lower cyclic ether organic solvent, a lower ketone organic solvent or a lower nitrile organic solvent at any ratio by volume, including, but not limited to the following mixed solvent systems and ratios: methanol/water (10:1, 5:1 or 3:1), ethanol/water (10:1, 5:1 or 3:1), acetonitrile/water (10:1, 5:1 or 3:1), tetrahydrofuran/water (10:1, 5:1 or 3:1), acetone/water (10:1, 8:1, 5:1, 4:1 or 3:1), 1,4-dioxane/water (10:1, 5:1 or 3:1), etc.

In the expression "a lower alcohol organic solvent, a lower cyclic ether organic solvent, a lower ketone organic solvent or a lower nitrile organic solvent" as used in the invention, the term "lower" means that an organic solvent has 1-6 carbon atoms in the molecule, preferably, an organic solvent has 1-4 carbon atoms.

The term "2θ angle" as used in the invention means that X-ray diffraction analysis is based on Bragg's law (Bragg's law is $2d \sin \theta = n\lambda$), wherein "θ" is the glancing angle or Bragg angle, i.e., the complementary angle for the angle of incidence, and "2θ" is the diffraction angle; "d" is the interplanar spacing between adjacent lattice planes in the crystal lattice, expressed as Å; "λ" is the wavelength of X-ray; and "n" is any positive integer, i.e., the "order" of diffraction. In the XRPD pattern, the abscissa of powder diffraction peaks is the 2θ angle, and the 2θ position of peak has a deviation of ±0.3°, preferably of ±0.2°. When the crystal form of the invention is determined by X-ray diffraction, sometimes there is a deviation in the measured peaks due to the measurement instrument or conditions. Therefore, when determining a crystal structure, the deviation shall be taken into account. Thus, when determining the degree of 2θ, a deviation of ±0.2 is employed by the applicant.

Differential scanning calorimetry (DSC) is a thermoanalytical technique. Within a programmed temperature range, the difference in power input (such as the amount of heat) required for a sample and reference is measured as a function of temperature. The curve recorded by differential scanning calorimeter is also called DSC curve, which uses heat absorption or heat release rate (heat flow dH/dt (unit: mJ/s)) as the ordinate, and uses temperature T or time t as the abscissa, and can be used to determine a lot of thermodynamic and kinetic parameters, for example, specific heat capacity, reaction heat, transition heat, phase diagram, reaction rate, crystallization rate, polymer crystallinity, sample purity, and so on. The method can be applied within a wide temperature range (−175~725° C.), and has a high resolution, and a small amount of sample is required.

Thermogravimetric Analysis (TGA) is a thermoanalytical technique that measures the mass of a test sample as the temperature changes within a programmed temperature range. It is used to study the thermal stability and composition of a substance. TGA measures the mass of a sample as the temperature (or time) changes within a programmed temperature range. When a test substance sublimes, vaporizes, decomposes or loses water of crystallization during heating, the mass of the test substance will change. In this case, the thermogravimetric curve is not a straight line, and drops to some extent. By analyzing the thermogravimetric curve, the temperature, at which the test substance changes, can be determined; and based on the lost weight, the lost substance such as water of crystallization can be determined by calculation. By conducting TGA experiments, it is helpful to study the change in nature of crystals, for example, physical phenomena of substances such as melting, evaporation, sublimation and adsorption; and is also helpful to study the chemical phenomena of substances, such as dissociation, oxidation, reduction, thermal stability, decomposition process, quantitative analysis of ingredients, effects of additives and fillers, moisture and volatiles, and reaction kinetics. Thermogravimetric analysis can be generally classified into two types: dynamic TGA (temperature increasing) and static TGA (isothermal). The curve obtained by thermogravimetric test is called the thermogravimetric curve (TG curve). TG curve uses mass as the ordinate (the mass reduces from top to bottom), and temperature (or time) as the abscissa (the temperature (or time) increases from left to right).

X-ray Powder Diffraction (XRPD) means that when a beam of X-rays reaches an object, it is scattered by the atoms in the object, each atom produces scattered waves, and these waves interfere with each other, resulting in diffraction. As a result of the superposition of scattered waves, the X-rays have the intensity enhanced in some directions, and weakened in other directions. The crystal structure can be obtained by analysis of diffraction results. X-ray diffractometer can accurately determine the crystal structure, texture and stress of a substance, and accurately achieve phase analysis, qualitative analysis, and quantitative analysis by utilizing diffraction theory. For crystal material, when the crystal to be measured is at different angles relative to the incident beam, those crystal faces satisfying the Bragg diffraction can be detected, which are presented by the diffraction peaks with different diffraction intensity in the XRD pattern. Non-crystal materials only have short-range ordered arrangement of several atoms in their structures, instead of long-range ordered arrangement of atoms in crystal structure. Therefore, non-crystal materials only have some diffuse scattering peaks in XRD pattern.

The invention further provides use of a crystal form of a compound of Formula (I) in manufacture of a medicament for treating a disease selected from hyperproliferative disease and chronic obstructive pulmonary disease.

The hyperproliferative disease according to the invention is selected from the group consisting of cancer and noncancerous disease; the cancer is selected from the group consisting of brain tumor, lung cancer, squamous epithelial cell cancer, bladder cancer, gastric cancer, ovarian cancer, peritoneal cancer, pancreatic cancer, breast cancer, head and neck cancer, cervical cancer, endometrial cancer, colorectal cancer, liver cancer, renal cancer, esophageal adenocarcinoma, esophageal squamous cell carcinoma, non-Hodgkin's lymphoma, central nervous system tumor, prostate cancer and thyroid cancer; the noncancerous disease is benign hyperplasia of skin or prostate.

The invention further provides a pharmaceutical formulation comprising the crystal form of a compound of Formula (I) and one or more pharmaceutically acceptable carriers and/or diluents, which may be any pharmaceutically acceptable dosage form, such as an oral formulation and an injection. When being prepared into an oral formulation, a suitable filler, a suitable binding agent, a suitable disintegrating agent or a suitable lubricant, etc. may be added.

The invention is further described, but is not restricted by the following embodiments. A person skilled in the art, based on the teachings of the invention, can make various modifications or improvements without departing from the basic spirit and scope of the invention.

EXPERIMENTAL SOLUTIONS

The exemplified experimental solutions are provided for a part of the compounds according to the invention in order to show the favorable activity and beneficial technical effects of the compounds according to the invention. However, it should be understood that the following experimental solutions are provided only for the purpose of describing the contents of the invention, rather than restricting the scope of the invention. A person skilled in the art, based on the teachings contained in the description, can make suitable modifications or improvements to the technical solutions of the invention without departing from the spirit and scope of the invention.

Experimental Example 1. Study on Solubility in Water

Test sample: Crystal form I and Crystal form II of dihydrochloride of a compound of Formula (I), the preparation methods of which could be found in the following Examples.

Experimental Method:
(1) Soluble property test: to a test sample, adding a corresponding solvent dropwise in a small amount for several times, shaking in a 25° C. thermostat water bath until the sample was completely dissolved, and calculating the dissolved concentration, i.e., soluble property.

(2) Solubility test: to a suitable volume of water, adding a test sample until oversaturation occurred in the solution of the sample, vortexing, centrifuging, filtrating the supernatant and then diluting it to a suitable concentration, subjecting the sample to a liquid chromatographic instrument, and determining the saturated concentration of the sample (i.e., saturated solubility) by external standard method.

Experimental Result:

TABLE 1

Soluble property of Crystal form I and Crystal form II

| Solvent | Soluble property (Solubility) | |
|---|---|---|
| | Crystal form I (mg/mL) | Crystal form II (mg/mL) |
| water | slightly soluble, (soluble property: 20) solubility: 39.14 | slightly soluble, (soluble property: 23.23) solubility: 28.94 |

As seen from the data in the Table 1, Crystal form I of dihydrochloride of a compound of Formula (I) was superior to Crystal form II in terms of soluble property in water, and could meet the requirement of druggability.

Experimental Example 2. Evaluation on Pharmacokinetics of Different Forms in Beagle Dogs Test sample: Crystal form I and Crystal form II of dihydrochloride of a compound of Formula (I), and an amorphous form of dihydrochloride of a compound of Formula (I), the preparation methods of which could be found in the following Examples.

Animal subject: beagle dogs, male, weighed 8~14 kg, 3 dogs/crystal form. Beagle dogs were purchased from Beijing Marshall Biotechnology Co. Ltd.

Experimental Method:
Administration: three test samples were prepared into capsules, at an administration dose of 3 mg/kg according to body weight of dog.

About 47.3 mg of Crystal form I was weighed, and packaged into hollow capsules (three capsules in total, one capsule per dog).

About 40.4 mg of Crystal form II was weighed, and packaged into hollow capsules (three capsules in total, one capsule per dog).

About 37.3 mg of an amorphous compound was weighed, and packaged into hollow capsules (three capsules in total, one capsule per dog).

Blood Collection:
Blood was collected 10 min, 30 min, 1 h, 2 h, 4 h, 6 h, 8 h, and 24 h after administration. Before blood collection, the animals were fixed, and whole blood (about 400 µL) was collected from vein of forelimb at each time point, and added to $K_2$EDTA-containing anticoagulation tubes. The whole blood sample was centrifuged for 6 min at 4° C., 8000 rpm in a high speed centrifuge, and plasma was separated. Plasma needed to be prepared within 30 min after blood collection, and plasma was stored at −80° C. in a refrigerator.

Plasma Sample Analysis:
The plasma samples were analyzed by protein precipitation: to plasma (50 µL), an internal standard Afatinib dimaleate (200 µL, 50 ng/mL acetonitrile solution) was added; the resultant mixture was vortexed at 1500 rpm for 3 min, and centrifuged at 12000 rpm for 5 min; to the supernatant (100 µL), water (100 µL) was added; the resultant mixture was mixed homogeneously under vortexing and analyzed by LC-MS/MS for blood concentration.

Calculation of PK parameter:

PK parameters were calculated by using Pharsight Phoenix 6.2 software.

Experimental Result:

TABLE 2

PK experimental data of different forms in beagle dogs

| Compound | Dose (mg/kg) | $T_{1/2}$ (h) | $T_{max}$ (h) | $C_{max}$ (ng/mL) | $AUC_{0-t}$ (h*ng/mL) | $AUC_{inf}$ (h*ng/mL) |
|---|---|---|---|---|---|---|
| Crystal form I | 3 | 4.95 | 2.00 | 15.3 | 112 | 115 |
| Crystal form II | 3 | 3.98 | 2.00 | 14.6 | 110 | 111 |
| Amorphous form | 3 | 2.47 | 2.00 | 16.6 | 68.6 | 79.9 |

$T_{1/2}$ represents drug elimination half-life, $T_{max}$ represents time to maximum blood concentration, $C_{max}$ represents maximum blood concentration, $AUC_{last}$ represents area under concentration-time curve from 0→t, $AUC_{inf}$ represents area under concentration-time curve from 0→∞.

It could be seen from the experimental result of Table 2 that as compared with the amorphous compound, both Crystal form I and Crystal form II had pharmacokinetic properties improved a lot, especially Crystal form I had longer half-life, and higher drug exposure, indicating that Crystal form I and Crystal form II had better druggability than the amorphous form.

Experimental Example 3. Study on Stability of Crystal Form I and Crystal Form II Test sample: Crystal form I and Crystal form II of dihydrochloride of a compound of Formula (I), the preparation methods of which could be found in the following Examples.

Method for Testing Crystal Form I:

A test sample was kept under influencing factor condition (a high temperature of 60° C.) for 30 d. Samples were separately taken at specified time points, and compared with the sample at Day 0. XRPD, relevant substances, contents, character, acidity, moisture content, and the like were determined. During the study, samples were packaged with plastic bags and sealed with aluminum foil outside.

Test samples were kept under accelerated condition (40° C.+RH 75%) for 6 months. Samples were separately taken at specified time points. XRPD, character, relevant substances, content, acidity, moisture content and the like were studied.

Test samples were kept under long-term condition (25° C.) for 6 months. Samples were separately taken at specified time points. Important items of stability (relevant substances) were studied.

At the last time point of the accelerated condition and long-term condition, XRPD, character, relevant substances, content, pH, moisture content and the like were studied.

Method for Testing Crystal Form II:

Test samples in culture dishes were left uncovered. The test samples, which were kept under influencing factor conditions (a high temperature of 60° C., 25° C.-high moisture RH 75%, and 25° C.-high moisture RH 92.5%, under the condition of light) for 5 days and 10 days, were studied for stability; and the test samples which were kept at 40° C. for 5 days, 10 days and 30 days, and the test samples which were kept at 25° C. for 30 days and 90 days, were studied for stability. Samples were separately taken at specified time points, and the items (moisture content (Coulomb), relevant substances, XRPD) were studied.

(1) Determination of Content

In accordance with High Performance Liquid Chromatography in Appendix V D in Pharmacopoeia of the People's Republic of China (2010), samples at Day 0 were used as control samples, and samples were determined by external standard method.

Operation Condition

Instrument: High Performance Liquid Chromatographic Instrument (Agilent 1200 series)

Chromatographic column: chromatographic column using octylsilane chemically bonded silica as filler (HC-$C_8$, 4.6×250 mm, 5 µm)

Column temperature: 30° C.

Mobile phase: mobile phase consisting of 0.03 mol/L diammonium hydrogen phosphate/0.01 mol/L sodium perchlorate solution-acetonitrile, and reversed-phase gradient elution was employed.

Flow rate: 1.0 mL/min

Injection volume: 10 µL

Detection wavelength: 254 nm (2) Relevant Substances

In accordance with High Performance Liquid Chromatography in Appendix V D in Pharmacopoeia of the People's Republic of China (2010), samples were determined by area normalization method.

Operation Condition

Instrument: High Performance Liquid Chromatographic Instrument (Agilent 1200 series)

Chromatographic column: chromatographic column using octylsilane chemically bonded silica as filler (HC-$C_8$, 4.6×250 mm, 5 µm)

Column temperature: 30° C.

Detection wavelength: 230 nm

Mobile phase: mobile phase consisting of 0.03 mol/L diammonium hydrogen phosphate/sodium perchlorate solution-acetonitrile, and reversed-phase isocratic elution was employed.

Flow rate: 1.0 mL/min

Injection volume: 10 µL (3) Moisture Content Determination

The moisture content was determined in accordance with First Method for Determining Moisture Content B (Coulometric Titration) in Appendix VIII M in Pharmacopoeia of the People's Republic of China (2010).

Experimental Result

TABLE 3

Result of stability of Crystal form I under influencing factor condition for 1 month

| Condition | Character | pH | Moisture content (%) | Content (%) | Relevant substances (%) | Crystal form XRPD |
|---|---|---|---|---|---|---|
| 0 day | light yellow powder | 2.8 | 3.9 | 100.8 | 0.15 | Crystal form I |
| 60° C.-covered-5 days | light yellow powder | 2.8 | 4.5 | 100.9 | 0.23 | Crystal form I |
| 60° C.-covered-10 days | light yellow powder | 2.7 | 4.5 | 100.7 | 0.24 | Crystal form I |
| 60° C.-covered-1 month | light yellow powder | 2.8 | 4.4 | 100.7 | 0.20 | Crystal form I |

TABLE 4

Result of stability of Crystal form I under accelerated condition and long-term condition for 1 month

| Condition | Character | pH | Moisture Content (%) | Content (%) | Relevant substances (%) | Crystal form XRPD |
|---|---|---|---|---|---|---|
| 0 day | light yellow powder | 2.8 | 3.9 | 100.8 | 0.15 | Crystal form I |
| 40° C. 1 month | light yellow powder | 2.8 | 4.6 | 100.9 | 0.19 | Crystal form I |
| 30° C. 1 month | light yellow powder | 2.8 | 4.3 | 100.8 | 0.18 | Crystal form I |
| 25° C. 1 month | light yellow powder | 2.8 | 4.2 | 100.7 | 0.18 | Crystal form I |

TABLE 5

Result of stability of Crystal form II under influencing factor condition

| Condition | Moisture content (%) | Relevant substances (%) | Crystal form XRPD |
|---|---|---|---|
| 0 day | 13.1 | 1.2 | Crystal form II |
| 40° C. 5 days | 4.5 | 1.3 | Crystal form I |
| 40° C. 10 days | 5.6 | 1.6 | Crystal form I |
| 40° C. 30 days | 5.3 | 3.0 | Crystal form I |
| 25° C. 30 days | 13.1 | 1.3 | Crystal form II |
| 25° C. 3 months | 13.4 | 1.3 | Crystal form II |
| 60° C. 5 days | 4.4 | 1.8 | Crystal form I |
| 60° C. 10 days | 5.3 | 2.3 | Crystal form I |
| Light 5 days | 13.2 | 1.5 | Crystal form II |
| Light 10 days | 13.3 | 1.8 | Crystal form II |
| RH92.5% 5 days | 13.4 | 1.2 | Crystal form II |
| RH92.5% 10 days | 13.5 | 1.3 | Crystal form II |
| RH75% 5 days | 13.2 | 1.3 | Crystal form II |
| RH75% 10 days | 13.3 | 1.3 | Crystal form II |

As seen from the data in Table 3 and Table 4, after Crystal form I of dihydrochloride of a compound of Formula (I) was kept at a high temperature of 60° C. (i.e., influencing factor condition) for 5 days, 10 days, and 1 month, there was no significant change in terms of relevant substances, content and crystal form, and there was almost no change in various studied items, i.e., the samples were stable; after keeping Crystal form I under accelerated condition and long-term condition for 1 month, there was no significant change in terms of relevant substances, content, and crystal form, and there was almost no change in various studies items, i.e., the samples were stable. Obviously, after Crystal form I of a compound of Formula (I) was kept under various conditions for 1 month, there was almost no change in various studied items, i.e., the samples were stable. Therefore, it could be determined that Crystal form I had high stability.

As seen from the data in Table 5, after Crystal form II of a compound of Formula (I) was kept at 40° C. for 5 days, 10 days, and 30 days, the moisture content reduced significantly, and was comparable to the moisture content of Crystal form I, and XRPD test showed that the Crystal form II was converted to Crystal form I; after keeping Crystal form II at 60° C. for 5 days and 10 days, the moisture content reduced significantly, and was comparable to the moisture content of Crystal form I, and XRPD test showed that the Crystal form II was converted to Crystal form I; under high moisture condition (RH92.5% and RH75%), there was no significant change in moisture content, and XRPD test showed that there was no change in crystal form; under the condition of light, there was no significant change in moisture content, and XRPD test showed that there was no change in crystal form. Therefore, it could be determined that Crystal form II was sensitive to high temperature conditions.

As seen from the experimental data in Tables 3-5, by studying influencing factor condition, accelerated condition and long-term condition, there was no significant change in terms of relevant substances, content, moisture content, acidity, XRPD, character and the like for Crystal form I, whereas Crystal form II had the moisture content, relevant substances, and XRPD changed to different extents, indicating that the stability of Crystal form I was higher than that of Crystal form II.

The above contents of the invention are further illustrated in detail by reference to the following examples. However, the invention should not be limited to the following examples. Any technologies belong to the scope of the invention as long as they can be accomplished based on the contents of the invention. The experimental methods, for which no concrete conditions are indicated in the following examples, are selected according to conventional methods and conditions, or the instructions of products.

Example 1 Preparation of Crystal Form I of Dihydrochloride of a Compound of Formula (I)

By the method as described in WO2012027960A1, a free base of a compound of Formula (I) was prepared. The free base (148 g) was suspended in water (618 ml), and 12 mol/L concentrated hydrochloric acid (48 ml) was slowly added dropwise. After the addition, the free base was dissolved under stirring, and crystal precipitation was performed for 8 h. After suction filtration, the filter cake was washed with water (20 ml×2), and dried at 35° C. in vacuum (a vacuum degree of −1.0×10³ KPa) for 4 h, to obtain a crude product. The crude product was recrystallized with acetone-water=3.4:1 (2250 ml) at 70° C. to yield a product (109 g). The product stirred in acetone: water=8:1 (1200 ml) at 25° C. for 24 h, was subjected to suction filtration, washed with acetone (200 ml), and dried at 35° C. in vacuum (a vacuum degree of −1.0×10³ KPa) for 6 h, to obtain Crystal Form I of dihydrochloride of a compound of Formula (I) (100.7 g).

The Crystal form I obtained was determined by X-ray diffraction under the following conditions:

Cu-Kα radiation, 1.54 Å (monochromator), determined by D/MAX-RB Type X-ray diffractometer.

Figure 8:
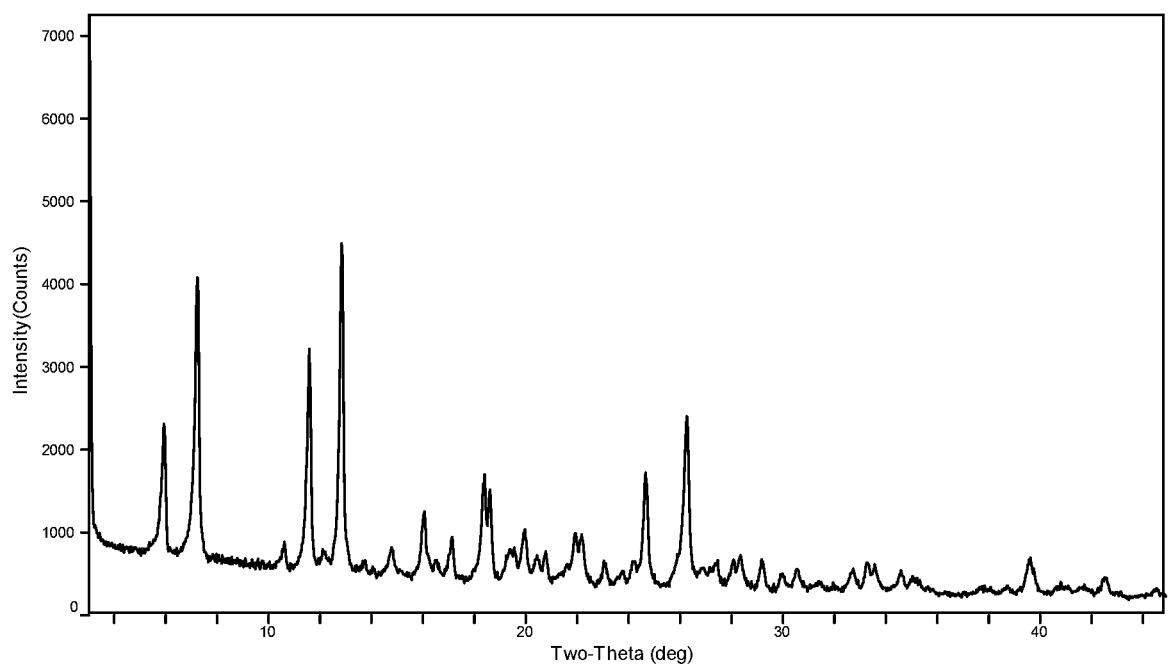
FIG. 8 shows the X-ray powder diffraction (XRPD) pattern of Crystal form I of dihydrochloride of the compound of Formula (I), wherein the ordinate represents diffraction intensity (CPS), and the abscissa represents the diffraction angle (2θ).

The XRPD pattern of Crystal form I was shown in FIG. 8. As seen from FIG. 8, Crystal form I had an X-ray powder diffraction pattern having characteristic peaks at the following 2θ positions: relatively strong characteristic peaks at the 2θ positions of 5.9, 7.2, 11.6, 12.8, 18.4, 24.7, and 26.3; characteristic peaks at the 2θ positions of 16.1, 18.7, 22.1; and characteristic peaks at the 2θ positions of 16.5, 20.0, 24.2, 28.1, 28.4, 29.2, and 39.6.

Example 2 Preparation I of Crystal Form II of Dihydrochloride of a Compound of Formula (I)

Crystal form I of dihydrochloride of a compound of Formula (I) (200 mg, 0.34 mmol) was put in a round-bottom flask, and water (1 mL) was added. After stirring for 10 h, a certain volume of solution was filtrated and dried to obtain light yellow crystal (solid), which was identified as Crystal form II by XRPD test.

① X-ray Powder Diffraction (XRPD)

The Crystal form II obtained was determined by X-ray diffraction under the following conditions:

Cu-Kα radiation, 1.54 Å (monochromator), determined by D/MAX-RB Type X-ray diffractometer.

Figure 2:
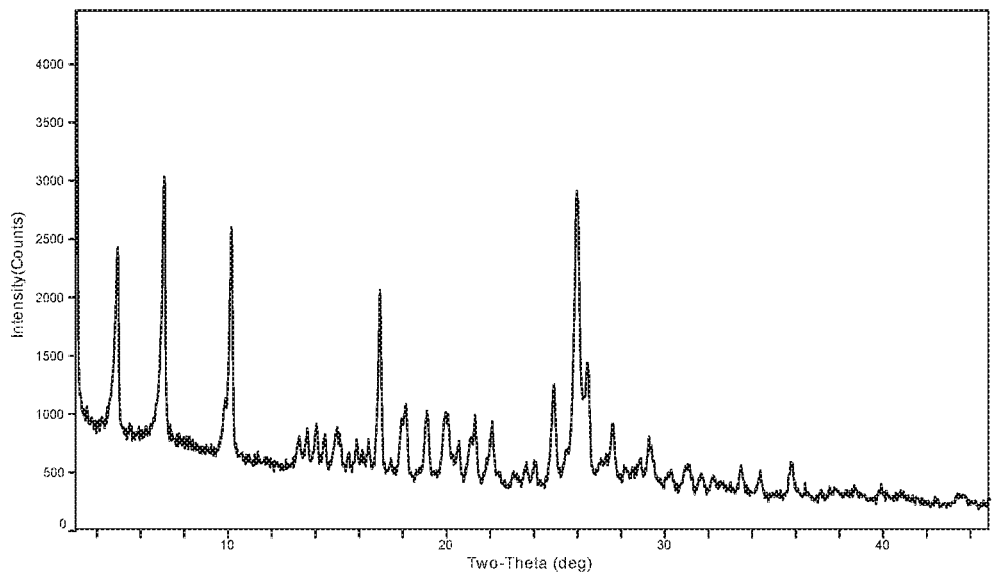
FIG. 2 shows the X-ray powder diffraction (XRPD) pattern of Crystal form II of dihydrochloride of a compound of Formula (I), wherein the ordinate represents diffraction intensity (CPS), and the abscissa represents the diffraction angle (2θ).

The XRPD pattern of Crystal form II was shown in FIG. 2. As seen from FIG. 2, Crystal form II had an X-ray powder diffraction pattern having characteristic peaks at the following 2θ positions: relatively strong characteristic peaks at the 2θ positions of 5.0, 7.0, 10.1, 17.0, 26.0, and 26.5; characteristic peaks at the 2θ positions of 10.1, 18.1, 19.1, 19.9, and 24.9; and characteristic peaks at the 2θ positions of 21.3, 22.1, 27.6, 29.3, and 35.8.

② DSC Test

The Crystal form II obtained was determined by DSC under the following conditions:

Instrument Type: TA Q2000 differential scanning calorimeter, under the protection of nitrogen, at a heating rate of 5° C./min.

Figure 5:
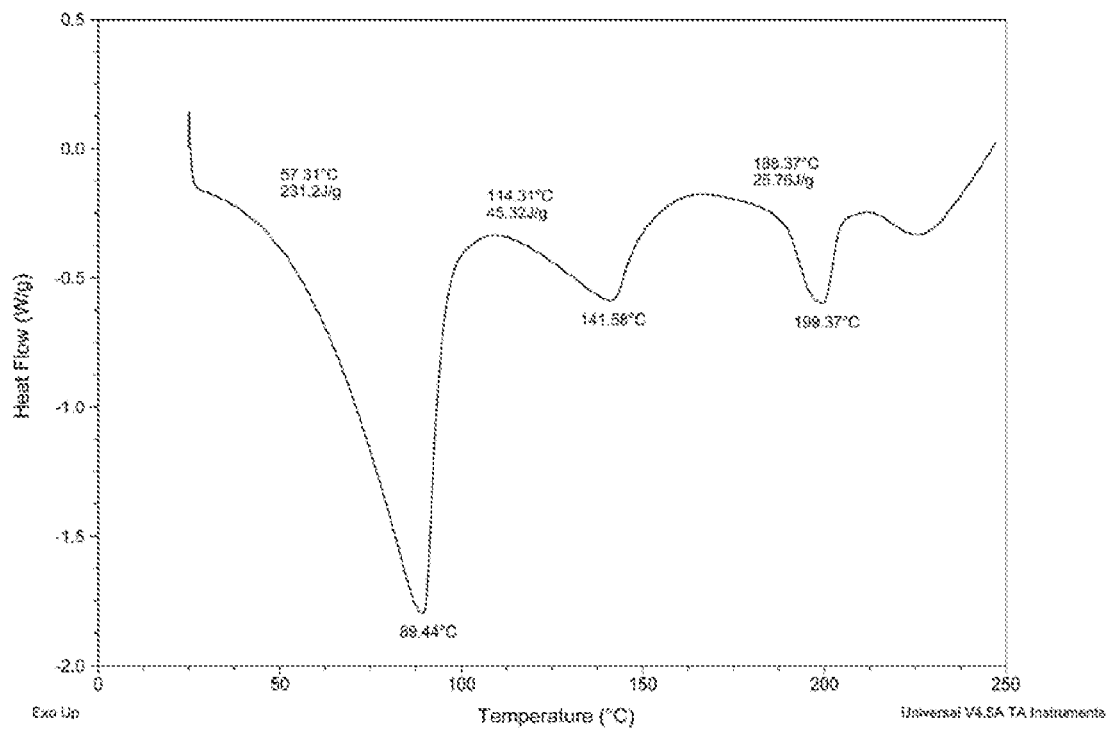
FIG. 5 shows the DSC thermogram of Crystal form II of dihydrochloride of a compound of Formula (I), wherein the ordinate represents heat flow (W/g), and the abscissa represents temperature (° C.).

The DSC thermogram of Crystal form II was shown in FIG. 5. As seen from FIG. 5, Crystal form II had a first endothermic conversion peak at 57-114.3° C., a second endothermic conversion peak at 114.5-175° C., and a third endothermic conversion peak at 188.4-199.4° C.

③ TGA Test (Determination of Water of Crystallization)

The Crystal form II obtained was determined by TGA under the following conditions:

Instrument Type: TA Q50, the testing condition: the temperature was increased to 350° C. at a rate of 10° C./min.

Figure 6:
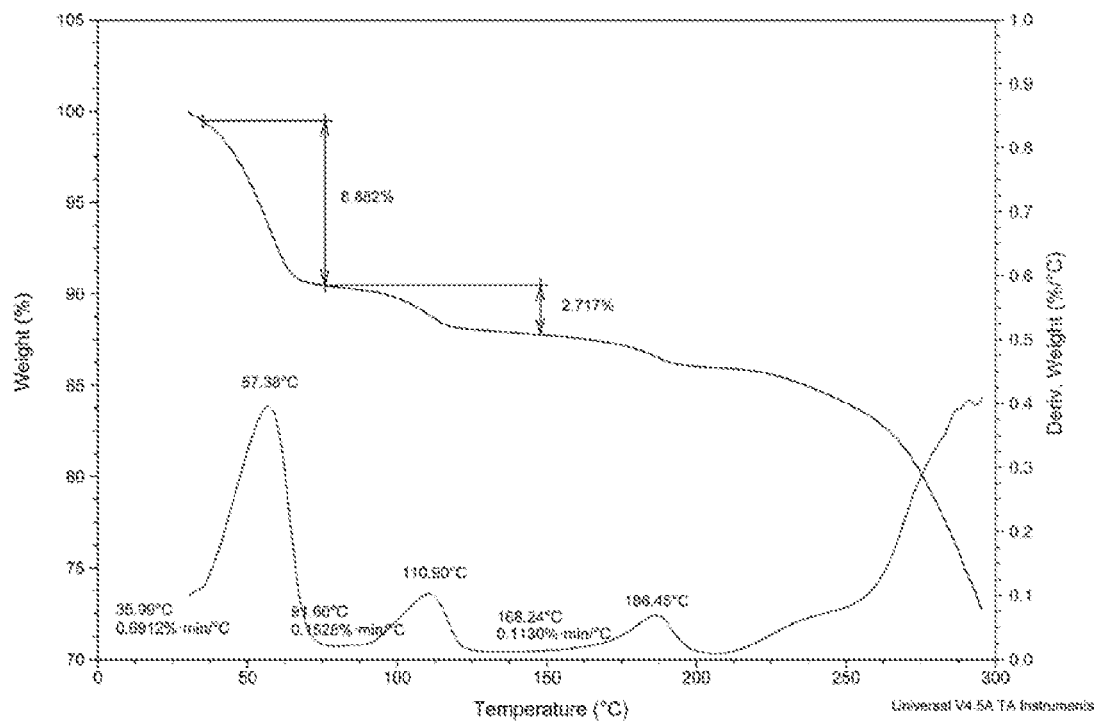
FIG. 6 shows the TGA thermogram of Crystal form II of dihydrochloride of a compound of Formula (I), wherein the ordinate represents mass percent (%), and the abscissa represents a complex coordinate time-temperature (° C.).

The TGA thermogram of Crystal form II was shown in FIG. 6. As seen from FIG. 6, Crystal form II had a dehydration percent of 8.882% at 57.38° C., and a dehydration percent of 2.717% at 110.90° C., which were close to the percent of a hydrate containing 3-5 molecules of water (i.e., 8.5%, 11.0%, and 13.4%) theoretically.

Example 3 Preparation II of Crystal Form II of Dihydrochloride of a Compound of Formula (I)

A free base of a compound of Formula (I) (577 g, 1.13 mol) was added to water (2.9 L), and concentrated hydrochloric acid (12 mol/L, 185 mL) was added. After complete dissolution, the solution was filtrated, and a small amount of seed crystal of Crystal form II was added to the filtrate. After stirring at 25° C. for 8 h, suction filtration was carried out. The filter cake was dried in vacuum at 35° C. for 20 h to obtain a yellow crystal (462 g, yield: 70.1%), which was identified as Crystal form II by XRPD test.

XRPD: having characteristic peaks at the following 2θ positions:

4.9, 7.0, 10.1, 16.9, 25.9, 26.4.

Example 4 Preparation III of Crystal Form II of Dihydrochloride of a Compound of Formula (I)

Crystal Form I of dihydrochloride of a compound of Formula (I) (200 mg, 0.34 mmol) was put in a round-bottom flask, and a mixed solvent of acetone (2 mL) and water (0.2 mL) was added. After stirring at room temperature for 4 days, the resultant mixture was filtrated to obtain a solid, which was identified as Crystal form II by XRPD test.

XRPD: having characteristic peaks at the following 2θ positions:

4.9, 7.1, 10.1, 17.0, 26.0, 26.5.

Example 5 Preparation IV of Crystal Form II of Dihydrochloride of a Compound of Formula (I)

Crystal Form I of dihydrochloride of a compound of Formula (I) (200 mg, 0.34 mmol) was put in a round-bottom flask, and a mixed solvent of ethanol (2 mL) and water (0.2 mL) was added. After stirring at room temperature for 40 h, the resultant mixture was filtrated to obtain a solid, which was identified as Crystal form II by XRPD test.

XRPD: having characteristic peaks at the following 2θ positions:

5.0, 7.2, 10.2, 17.1, 26.1, 26.6.

Example 6 Preparation V of Crystal Form II of Dihydrochloride of a Compound of Formula (I)

Crystal Form I of dihydrochloride of a compound of Formula (I) (200 mg, 0.34 mmol) was put in a round-bottom flask, and a mixed solvent of acetonitrile (2 mL) and water (0.2 mL) was added. After stirring at room temperature for 40 h, the resultant mixture was filtrated to obtain a solid, which was Crystal form II by XRPD test.

XRPD: having characteristic peaks at the following 2θ positions:

5.0, 7.2, 10.2, 17.1, 26.1, 26.6.

Example 7 Preparation VI of Crystal Form II of Dihydrochloride of a Compound of Formula (I)

To Crystal Form I of dihydrochloride of a compound of Formula (I) (295 g, 0.51 mmol), a mixed solvent of acetone (3587 mL) and water (1043 mL) was added. After stirring at 60° C. under reflux for about 2 h, there was still a small amount of crystal undissolved. The temperature was reduced continuously, and when the temperature was reduced to 40° C., the seed crystal of Crystal form II (1.5 g) was added. After filtration, the filter cake was washed with a mixed solvent (acetone:water=4:1, 300 mL), and then washed with acetone (300 mL) twice, to obtain a solid, which was identified as Crystal form II by XRPD test.

XRPD: having characteristic peaks at the following 2θ positions:

5.0, 7.2, 10.2, 17.1, 26.1, 26.6.

Example 8 Preparation VII of Crystal Form II of Dihydrochloride of a Compound of Formula (I)

Crystal Form I of dihydrochloride of a compound of Formula (I) (100 mg, 0.17 mmol) was put in a round-bottom flask, and a mixed solvent of methanol (1 mL) and water (0.1 mL) was added. After stirring at room temperature for 24 h, centrifugation was performed and the supernatant was discarded. After drying at 30° C. in vacuum for 1.5 h, the XRPD pattern was determined, which showed that the product was Crystal form II.

After replacing methanol with isopropanol, n-butanol, tetrahydrofuran, or dioxane, Crystal form II was also obtained under the same experimental conditions and operations.

XRPD: having characteristic peaks at the following 2θ positions:
5.0, 7.2, 10.2, 17.1, 26.1, 26.6.

Example 9 Preparation of Crystal Form I of Dihydrochloride of a Compound of Formula (I)

The Crystal form II (10 g, 0.02 mol) was put in a culture dish with an inner radius of 8.8 cm (an area of 60.8 cm$^2$), and the dish was placed in a vacuum drying oven. Vacuum drying was carried out at −1.0×10$^3$ KPa, 35-40° C., and the drying agent was granular calcium chloride (20 g). Samples were taken every hour, and were determined for water content and XRPD pattern. 5 hours later, Crystal form II was completely converted to Crystal form I.

① X-ray Powder Diffraction (XRPD)

The Crystal form I obtained was determined by X-ray diffraction under the following conditions:

Cu-Kα radiation, 1.54 Å (monochromator), determined by D/MAX-RB Type X-ray diffractometer.

The XRPD pattern of Crystal form I was shown in FIG. 1. As seen from FIG. 1, Crystal form I had an X-ray powder diffraction pattern having characteristic peaks at the following 2θ positions: relatively strong characteristic peaks at the 2θ positions of 6.0, 7.3, 11.7, 12.9, 18.4, 24.7, and 26.3; characteristic peaks at the 2θ positions of 16.0, 18.7, and 21.9; and characteristic peaks at the 2θ positions of 16.6, 20.0, 24.3, 28.1, 28.5, 29.2, and 39.6.

② DSC Test

The Crystal form I obtained was determined by DSC under the following conditions:

Instrument Type: TA Q2000 differential scanning calorimeter, under the protection of nitrogen, at a heating rate of 5° C./min.

Figure 3:
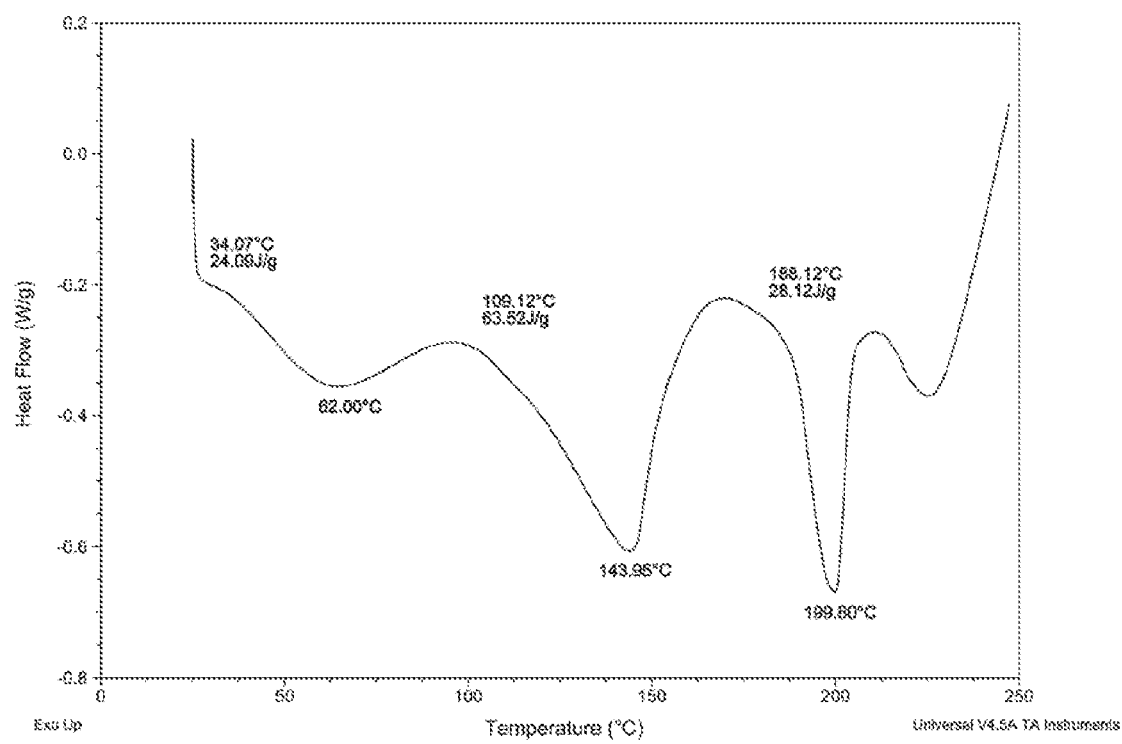
FIG. 3 shows the DSC thermogram of Crystal form I of dihydrochloride of a compound of Formula (I), wherein the ordinate represents heat flow (W/g), and the abscissa represents temperature (° C.).

The DSC thermogram of Crystal form I was shown in FIG. 3. As seen from FIG. 3, Crystal form I had a first endothermic conversion peak at 109-188.5° C., and a second endothermic conversion peak at 188.5-215° C.

③ TGA Test (Determination of Water of Crystallization)

The Crystal form I obtained was determined by TGA under the following conditions: Instrument Type: TA Q50, under the protection of nitrogen, the testing condition: the temperature was increased to 350° C. at a rate of 10° C./min.

Figure 4:
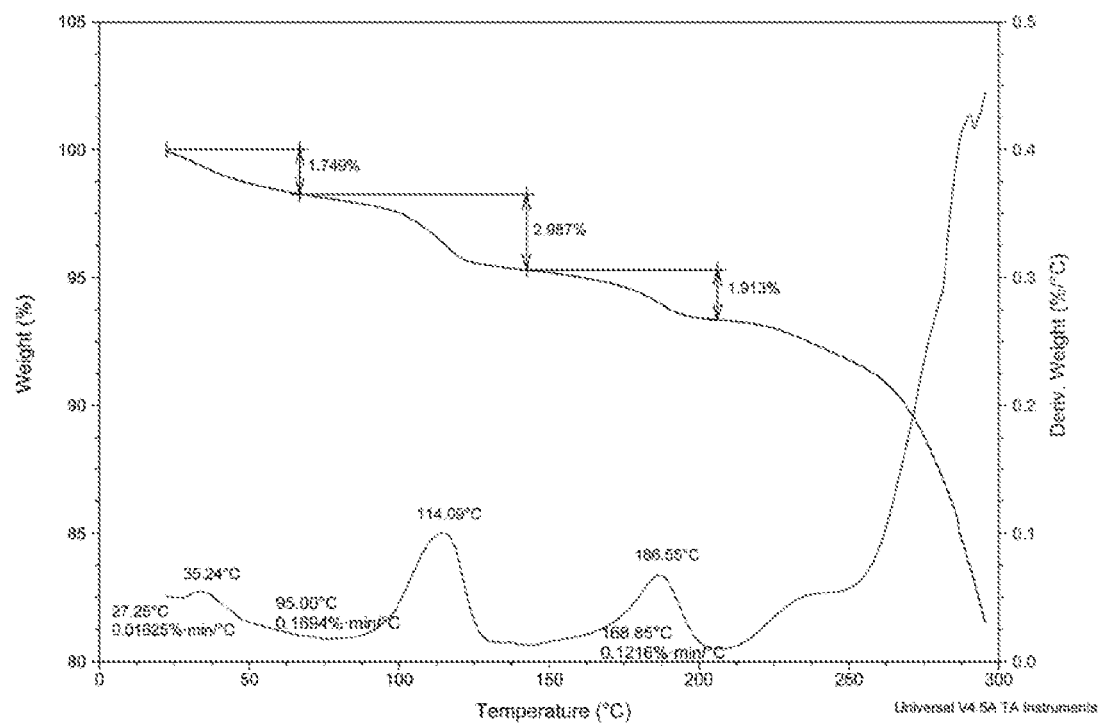
FIG. 4 shows the TGA thermogram of Crystal form I of dihydrochloride of a compound of Formula (I), wherein the ordinate represents mass percent (%), and the abscissa represents a complex coordinate time-temperature (° C.).

The TGA thermogram of Crystal form I was shown in FIG. 4. As seen from FIG. 4, Crystal form I had a dehydration percent of 2.987% at 114.09° C., which was close to the percent 3.0% of a hydrate containing 1 molecule of water theoretically.

Example 10 Preparation of an Amorphous Form of Dihydrochloride of a Compound of Formula (I)

Figure 7:
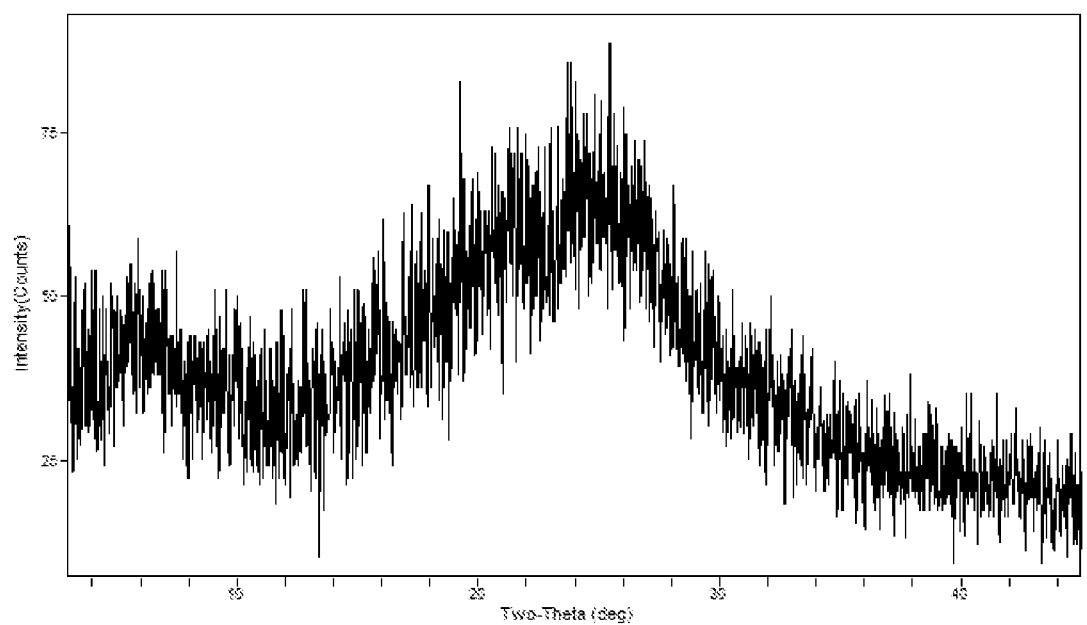
FIG. 7 shows the X-ray powder diffraction (XRPD) pattern of an amorphous form of dihydrochloride of a compound of Formula (I), wherein the ordinate represents diffraction intensity (CPS), and the abscissa represents the diffraction angle (2θ).

Crystal form II of dihydrochloride of a compound of Formula (I) (150 mg, 0.26 mmol) was dissolved in methanol (10 mL). After the solid was dissolved, the solution was concentrated under reduced pressure to obtain a solid powder. Since XRPD test showed no characteristic peak, it was identified as an amorphous form (see FIG. 7).

The invention claimed is:

1. Crystal form I of dihydrochloride of N-(4-((3-chloro-4-fluorophenyl)amino)-7-((7-methyl-7-azaspiro[3.5]nonan-2-yl)methoxy)quinazolin-6-yl)acrylamide represented by Formula (I), wherein the Crystal form I exhibits an X-ray powder diffraction pattern having characteristic peaks at the 2θ positions of 6.0±0.2°, 7.3±0.2°, 11.7±0.2°, 12.9±0.2°, 18.4±0.2°, 24.7±0.2°, and 26.3±0.2°, as determined by using Cu-Kα radiation,

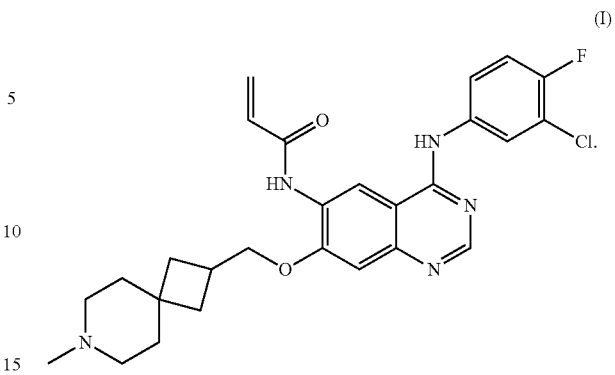

2. The Crystal form I according to claim 1, wherein the X-ray powder diffraction pattern further has characteristic peaks at the 2θ positions of 16.0±0.2°, 18.7±0.2°, and 21.9±0.2°, as determined by using Cu-Kα radiation.

3. The Crystal form I according to claim 2, wherein the X-ray powder diffraction pattern further has characteristic peaks at the 2θ positions of 16.6±0.2°, 20.0±0.2°, 24.3±0.2°, 28.1±0.2°, 28.5±0.2°, 29.2±0.2°, and 39.6±0.2°, as determined by using Cu-Kα radiation.

4. The Crystal form I according to claim 1, which exhibits a differential scanning calorimetry (DSC) thermogram having a first endothermic conversion peak at 109-188.5° C., and a second endothermic conversion peak at 188.5-215° C.

5. The Crystal form I according to claim 1, which is a hydrate having a water content of 2%-3.5%.

6. The Crystal form I according to claim 1, which is a monohydrate.

7. Crystal form II of dihydrochloride of N-(4-((3-chloro-4-fluorophenyl)amino)-7-((7-methyl-7-azaspiro[3.5]nonan-2-yl)methoxy)quinazolin-6-yl)acrylamide represented by Formula (I), wherein the Crystal form II exhibits an X-ray powder diffraction pattern having characteristic peaks at the 2θ positions of 5.0±0.2°, 7.0±0.2°, 10.1±0.2°, 17.0±0.2°, 26.0±0.2°, and 26.5±0.2°, as determined by using Cu-Kα radiation,

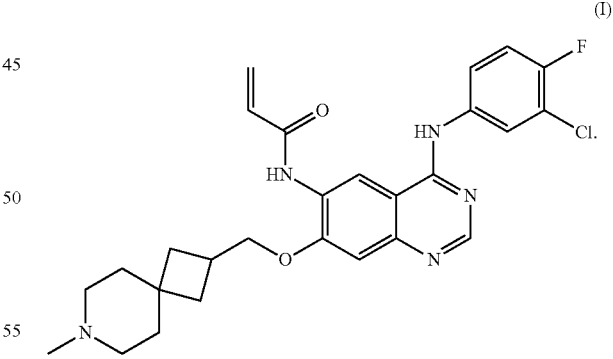

8. The Crystal form II according to claim 7, wherein the X-ray powder diffraction pattern further has characteristic peaks at the 2θ positions of 10.1±0.2°, 18.1±0.2°, 19.1±0.2°, 19.9±0.2°, and 24.9±0.2°, as determined by using Cu-Kα radiation.

9. The Crystal form II according to claim 8, wherein the X-ray powder diffraction pattern further has characteristic peaks at the 2θ positions of 21.3±0.2°, 22.1±0.2°, 27.6±0.2°, 29.3±0.2°, and 35.8±0.2°, as determined by using Cu-Kα radiation.

10. The Crystal form II according to claim 7, which exhibits a DSC thermogram having a first endothermic conversion peak at 57-114.3° C., a second endothermic conversion peak at 114.5-175° C., and a third endothermic conversion peak at 188.4-199.4° C.

11. The Crystal form II according to claim 7, which is a hydrate having a water content of 8.5%-14%.

12. The Crystal form II according to claim 7, which is a hydrate containing 3-5 molecules of water.

13. A method for preparing the Crystal form II according to claim 7, comprising the following steps: N-(4-((3-chloro-4-fluorophenyl)amino)-7-((7-methyl-7-azaspiro[3.5]nonan-2-yl)methoxy)quinazolin-6-yl)acrylamide is dissolved in water or in a mixed solvent of water and an organic solvent, and subjected by addition of concentrated hydrochloric acid to produce a solution, then the solution was filtrated and dried to obtain Crystal form II.

14. A method for preparing the Crystal form I according to claim 1, comprising the step of drying the Crystal form II in vacuum to obtain the Crystal form I.

15. A method for preparing the Crystal form II according to claim 7, comprising the following steps: Crystal form I is dissolved in water or in a mixed solvent of water and an organic solvent to produce a solution, then the solution was filtrated and dried to obtain the Crystal form II.

16. The method according to claim 13, wherein the organic solvent is selected from the group consisting of a lower alcohol organic solvent, a lower cyclic ether organic solvent, a lower ketone organic solvent or a lower nitrile organic solvent.

17. The method according to claim 16, wherein the lower alcohol organic solvent is selected from the group consisting of methanol, ethanol, isopropanol and n-butanol; the lower cyclic ether organic solvent is selected from the group consisting of tetrahydrofuran and dioxane; the lower ketone organic solvent is acetone; and the lower nitrile organic solvent is acetonitrile.

18. A pharmaceutical formulation, comprising the Crystal form I according to claim 1, and one or more pharmaceutically acceptable carriers and/or diluents.

19. A method for treating a disease selected from hyperproliferative disease and chronic obstructive pulmonary disease, comprising the step of administering to a subject in need thereof the Crystal form I according to claim 1;
wherein the hyperproliferative disease is selected from the group consisting of brain tumor, lung cancer, bladder cancer, gastric cancer, ovarian cancer, pancreatic cancer, breast cancer, head and neck cancer, colorectal cancer, renal cancer, esophageal adenocarcinoma, esophageal squamous cell carcinoma and prostate cancer.

20. The method according to claim 15, wherein the organic solvent is selected from the group consisting of a lower alcohol organic solvent, a lower cyclic ether organic solvent, a lower ketone organic solvent or a lower nitrile organic solvent;
wherein the lower alcohol organic solvent is selected from the group consisting of methanol, ethanol, isopropanol and n-butanol; the lower cyclic ether organic solvent is selected from the group consisting of tetrahydrofuran and dioxane; the lower ketone organic solvent is acetone; and the lower nitrile organic solvent is acetonitrile.

* * * * *